United States Patent [19]
Kida et al.

[11] Patent Number: 5,221,613
[45] Date of Patent: Jun. 22, 1993

[54] IMMUNOASSAY PROCESS AND LIQUID REAGENTS USED THEREFOR

[75] Inventors: Masaaki Kida, Suita; Kazunisa Kubotsu, Osaka; Shuji Matuura, Kawanishi, all of Japan

[73] Assignee: Wako Pure Chemical Industries Ltd., Osaka, Japan

[21] Appl. No.: 473,534

[22] Filed: Feb. 1, 1990

[30] Foreign Application Priority Data

Feb. 6, 1989 [JP] Japan .................................. 1-27122

[51] Int. Cl.$^5$ ................. G01N 33/535; G01N 33/543
[52] U.S. Cl. .................................. 435/7.93; 435/7.9; 435/975; 436/518; 436/808; 436/821; 436/829
[58] Field of Search ............... 436/518, 528, 535, 821, 436/829, 808; 435/7.9, 7.93, 975

[56] References Cited

U.S. PATENT DOCUMENTS

| | | | |
|---|---|---|---|
| 4,342,826 | 8/1982 | Cole | 435/7.9 |
| 4,565,696 | 1/1986 | Heath et al. | 424/88 |
| 4,581,222 | 4/1986 | Baldeschwieler et al. | 424/1.1 |
| 4,861,597 | 8/1989 | Kida et al. | 424/450 |

FOREIGN PATENT DOCUMENTS

| | | |
|---|---|---|
| 0-007714 | 2/1980 | European Pat. Off. . |
| 0-047480 | 3/1982 | European Pat. Off. . |
| 0-180980 | 5/1986 | European Pat. Off. . |
| 0212989 | 3/1987 | European Pat. Off. . |
| 0243001 | 10/1987 | European Pat. Off. . |
| 60-117159 | 6/1985 | Japan . |
| 2069133A | 8/1991 | United Kingdom . |
| WO86/04682 | 8/1986 | World Int. Prop. O. . |

OTHER PUBLICATIONS

Bangham et al., J. Mol. Biol., 13, 238 (1965).
J. H. Fendler, "Membrane Mimetic Chemistry", John Wiley & Sons, NY (1982).
C. Huang et al., Biochemistry, 8, 344 (1969).
F. Szoka et al., Proc. Natl. Acad. Sci., U.S.A., 75, 4194 (1978).
S. Batzri et al., Biochem. Biophs. Acta., 298, 1015 (1973).
D. Deamer et al., Biochim. Biophs. Acta., 443, 629 (1976).
J. R. Slack et al., Biochim. Biophys. Acta., 323, 547 (1973).
Biochemical et Biophysical Acta., 812, 116 (1985).
Biochemical et Biophysical Acta., 640, 66 (1981).
Journal of Immunological Methods, 75, 351 (1984).
Biochemical & Biophysical Research Communications, 117, 399 (1983).
Biochemical and Biophysical Research Communications, 89, 1114 (1979).
Liposome Technology, 29 (1983), CRC Press.
Ann. Rev. Biophys. Bioeng, 9, 467 (1980).
Sigma, pp. 1685-1687 (1990).
Braman et al., Bio/Technology 349-355 (Apr. 1984).
Six et al., 13 Biochemistry 4050-4053 (1974) (not entire article).

Primary Examiner—Esther L. Kepplinger
Assistant Examiner—Susan C. Wolski
Attorney, Agent, or Firm—Armstrong, Westerman, Hattori, McLeland & Naughton

[57] ABSTRACT

A combination of reagents including (i) a first liquid containing (a) first microcapsules having an analyte immobilized on surfaces thereof and containing a marker therein and (b) microcapsules encapsulating an antibody and having different capsule walls from said first analyte immobilized microcapsules with respect to susceptibility to a capsule wall lysin, and (ii) a second liquid containing complement is suitable for immunoassay based on complement-dependent immune lysis of microcapsules.

9 Claims, 1 Drawing Sheet

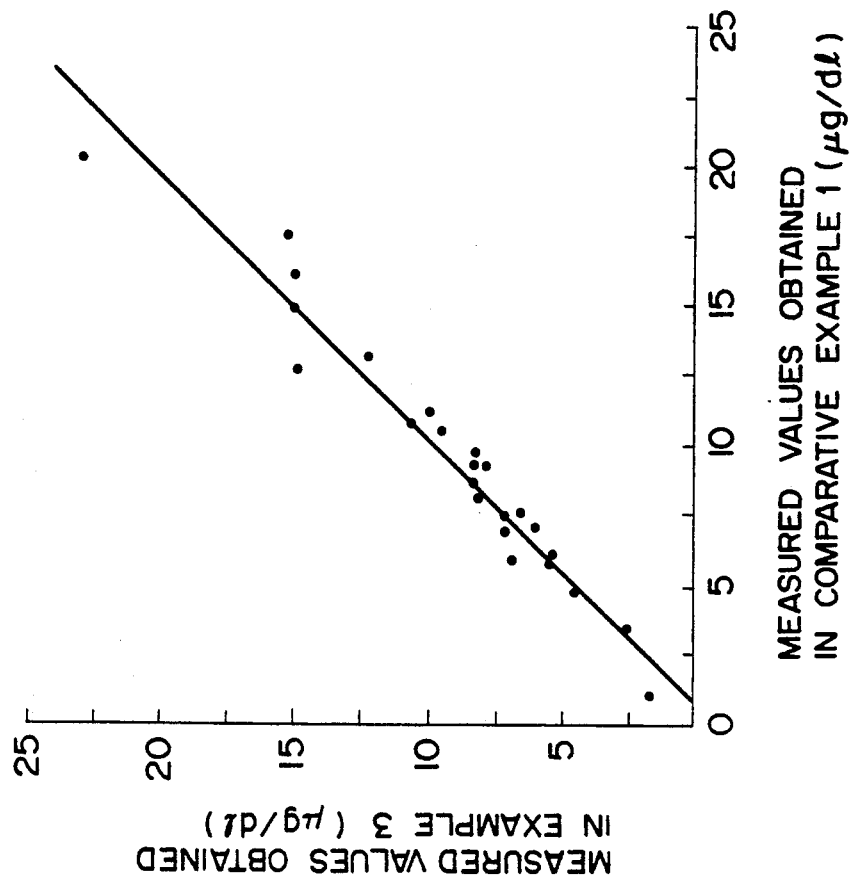
FIG. 2
FIG. 1
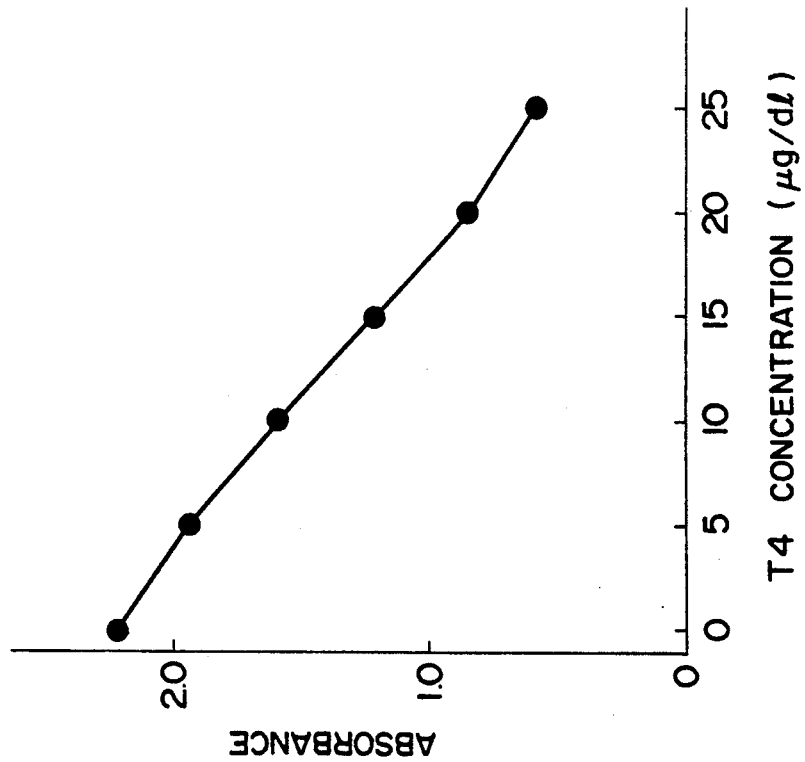

IMMUNOASSAY PROCESS AND LIQUID REAGENTS USED THEREFOR

BACKGROUND OF THE INVENTION

The present invention relates to a modification of an immunoassay based on complement-dependent immune lysis of microcapsules and liquid reagents used therefor which have been stabilized and can be used in autoanalyzers.

Immunoassay is a measuring method utilizing antigen-antibody reaction and is widely used, for example, as a method for measuring trace components in body fluids specifically.

As immunoassays which are now generally often used, there may be exemplified radioimmunoassay (RIA), enzyme immunoassay (EIA), etc. These method permit quantitative measurement of trace components in samples but involve individual problems. That is, RIA is disadvantageous, for example, in that since isotopes should be used therein, RIA requires special facilities and troublesome disposal of wastes. EIA is disadvantageous, for example, in that it requires a relatively long measurement time and is difficult to apply to an autoanalyzer.

Therefore, as an immunoassay involving none of these problems, there has recently been proposed and noted an immunoassay based on complement-dependent immune lysis of microcapsules.

A typical example of this method is a method using microcapsules (e.g. lipid film vehicles (liposomes)) having an analyte to be measured on surfaces thereof and containing a marker (e.g. enzyme) therein (hereinafter abbreviated as "labeled microcapsules") (hereinafter abbreviated as "immunoassay method based on complement-dependent immune lysis of microcapsules") (Japanese Patent Appln. Kokai No. 56-132564, U.S. Pat. No. 4,342,826). This method is as follows. A sample, labeled microcapsules, and an antibody to an analyte to be measured are fixed to carry out the antigen-antibody reaction, after which complement is added. The complement is activated by an antigen-antibody complex formed on the surfaces of the labeled microcapsules and lyses the membrane walls of the microcapsules to liberate a marker from the labeled microcapsules. The amount of analyte to be measured in the sample is determined on the basis of the amount of the marker liberated. This immunoassay method based on complement-dependent immune lysis of microcapsules induced by antigen-antibody reaction and hence makes it possible not only to measure a slight amount of an analyte to be measured, specifically, but also to carry out a series of reactions in a uniform reaction system. Therefore, it permits simpler and more rapid measurement than do conventional methods such as RIA and EIA.

This method is, however, difficult to apply to an autoanalyzer, in particular, an autoanalyzer using two liquid reagents which is now a leading autoanalyzer, and substantially no case has been reported for application of the method to such an autoanalyzer. The cause of this is that when the reagents (labeled microcapsules, antibody to an analyte to be measured, and complement) used in said method are stored in a proper combination in two liquid reagents, the stability of the liquid reagents is not sufficient.

When the three main reagents used in said method are divided between and stored in two liquid reagents, the following three combinations are thought of:

a) a combination of a mixed solution of complement and labeled microcapsules, and an antibody solution, b) a combination of a mixed solution of complement and antibody, and a solution of labeled microcapsules, c) a combination of a mixed solution of labeled microcapsules, and an antibody, and complement solution.

Whichever combination among them is employed for preparing liquid reagents, the resulting liquid reagents have a low stability during storage and hence are of no practical use. For example, in the case of the combination of a), the complement is inactivated by the interaction between the labeled microcapsules and the complement which coexist in the liquid reagent, so that immunolysis is gradually reduced. In the case of the combination of b), when an analyte to be measured is a substance which is unlikely to get mixed in a solution of complement derived from an animal, for example, a drug, the resulting liquid reagent is stable to a certain extent. But when it is a substance which is very likely to exist in a solution of complement, for example, hormone or tumor marker, the antigen-antibody reaction and inactivation of the complement occur in the mixed solution of the complement and the antibody, so that the stability of this liquid reagent is lowered. In the case of the combination of c), an analyte to be measured (an antigen) fixed on the labeled microcapsules reacts with the antibody previously, resulting in lowering of the measurement sensitivity. Therefore, depending on an analyte to be measured, there is now often no choice but to use three liquid reagents for an immunoassay method based on complement-dependent immune lysis of microcapsules. Accordingly, there has been an eager desire for the advent of liquid reagents for immunoassay method based on complement-dependent immune lysis of microcapsules and using two liquid reagents which can be used in autoanalyzers.

SUMMARY OF THE INVENTION

The present invention was made in consideration of such conditions and is intended to provide an immunoassay method based on complement-dependent immune lysis of microcapsules and using two liquid reagents, and liquid reagents used therefor having a high stability during storage, which are applicable to autoanalyzers.

The present invention provides a liquid reagent used for immunoassay method based on complement-dependent immune lysis of microcapsules comprising (a) first microcapsules having an analyte on surfaces thereof and containing a marker therein (i.e. labeled microcapsules), and (b) second microcapsules having different capsule walls from said first analyte immobilized microcapsules with respect to susceptibility to a capsule wall lysin and encapsulating an antibody specific to such analyte.

The present invention also provides an immunoassay reagent combination used for immunoassay method based on complement-dependent immune lysis of microcapsules comprising (i) a first liquid comprising (a) first microcapsules having an analyte immobilized on surfaces thereof and containing a marker therein, and (b) second microcapsules having different capsule walls from said first analyte immobilized microcapsules with respect to susceptibility to a capsule wall lysin and encapsulating an antibody specific to said analyte, and (ii) a second liquid containing complement.

The present invention further provides an immunoassay method based on complement-dependent immune lysis of microcapsules comprising a first step of reacting a sample containing an analyte and a capsule wall lysin with a first liquid comprising (a) first microcapsules having an analyte immobilized on surfaces thereof and containing a marker therein, and (b) second microcapsules having different capsule walls from said first analyte immobilized microcapsules with respect to susceptibility to a capsule wall lysin and encapsulating an antibody specific to said analyte, a second step of reacting the resulting reaction solution with a second liquid containing complement, and a third step of measuring the amount of the marker liberated by the second step.

BRIEF DESCRIPTION OF THE DRAWINGS

FIG. 1 shows a calibration curve for T4 obtained in Example 1.

FIG. 2 shows a correlational graph prepared on the basis of measured values obtained by Example 3 and Comparative Example 1.

DESCRIPTION OF THE PREFERRED EMBODIMENTS

According to the present invention, there is provided ① a liquid reagent used for immunoassay method based on complement-dependent immune lysis of microcapsules comprising an antibody to an analyte to be measured which is encapsulated in microcapsules which have different capsule walls from labeled microcapsules with respect to susceptibility to a capsule wall lysin.

There is further provided ② an immunoassay reagent combination used for immunoassay method based on complement-dependent immune lysis of microcapsules comprising (i) a first liquid comprising labeled microcapsules and microcapsules having different capsule walls from the labeled microcapsules with respect to susceptibility to a capsule wall lysin and encapsulating an antibody, and (ii) a second liquid containing complement.

There is still further provided an immunoassay method based on complement-dependent immune lysis of microcapsules comprising a first step of reacting a sample containing an analyte and a capsule wall lysin with a first liquid comprising (a) labeled microcapsules and (b) microcapsules having different capsule walls from said labeled microcapsules (a) with respect to susceptibility to a capsule wall lysin and encapsulating an antibody, a second step of reacting the resulting reaction solution with a second liquid containing complement, and a third step of measuring the amount of the marker liberated by the second step.

In the course of earnest study for finding an immunoassay method based on complement-dependent immune lysis of microcapsules which is applicable to autoanalyzers, we, the present inventors, found that the microcapsule lysing properties of various substances having a cell membrane lysing activity (i.e. "capsule wall lysin") vary depending on the constituents of microcapsule wall and its preparation method. We noticed this point and further investigated. Consequently, we found that an immunoassay method based on complement-dependent immune lysis of microcapsules and using two liquid reagents which have a high stability during storage and can be used in antoanalyzer, can be constituted by using an antibody used in immunoassay methods based on complement-dependent immune lysis of microcapsules, after encapsulating the antibody in microcapsules which are more easily lysed by a specific capsule wall lysin, i.e., a surfactant, than labeled microcapsules. Thus, we accomplished the present invention. That is, the liquid reagent combination of this invention comprises a first liquid comprising labelled microcapsules and microcapsules characterized by encapsulating an antibody (hereinafter abbreviated as "encapsulated antibody"), and a second liquid containing complement.

As the specific capsule wall lysin used in the measuring process of this invention, surfactants can be exemplified. The capsule wall lysin is not critical so long as it lyses the capsule wall of encapsulated antibody but not the capsule wall of labeled microcapsules, and does not affect the measurement. As such surfactants, the following can be exemplified. Nonionic surfactants, for example, polyoxyethylene alkyl ethers such as polyoxyethylene cetyl ether, polyoxyethylene lauryl ether, etc.; polyoxyethylene alkylphenyl ethers such as polyoxyethylene otylphenyl ether, etc.; polyoxyethylene alkyl esters such as polyoxyethylene sorbitan monooleate, polyoxyethylene sorbitan monopalmitate, polyoxyethylene sorbitan monostearate, polyoxyethylene sorbitan triolate, etc.; methylglucamide derivatives such as octanoyl-N-methylglucamide, nonanoyl-N-methylglucamide, decanoyl-N-methylglucamide, etc.; and alkyl sugar derivatives such as n-octyl-$\beta$-D-glucoside, etc. Anionic surfactants, for example, sodium dodecyl sulfate (SDS), laurylbenzenesulfonic acid, deoxycholic acid, cholic acid, tris(hydroxymethyl)aminomethane dodecylsulfite (Tris DS), etc. Cationic surfactants, for example, alkylamine salts such as octadecylamine acetic acid salt, tetradecylamine acetic acid salt, stearylamine acetic acid salt, laurylamine acetic acid salt, lauryldiethyanolamine acetic acid salt, etc.; quaternary ammonium salts such as octadecyltrimethylammonium chloride, dodecyltrimethylammonium chloride, cetyltrimethylammonium chloride, cetyltrimethylammonium bromide, lauryltrimethylammonium chloride, allyltrimethylammonium methylsufate, benzalkonium chloride, tetradecyldimethylbenzylammonium chloride, octadecyldimethylbenzylammonium chloride, lauryldimethylbenzylammonium chloride, etc.; and alkylpyridinium salts such as laurylpyridinium chloride, stearylamidomethylpyridinium chloride, etc. Amphoteric surfactants, for example, 3-[(3-cholamidoamidopropyl)dimethylammonio]-1-propane sulfonate, 3-[(3-cholamidoamidopropyl)dimethylammonio]-2-hydroxy-1-propane sulfonate, etc. Natural surfactants, for example, saponin (derived from soybean), and digitonin. The using concentration of these surfactants is not critical so long as they dissolve the capsule wall of encapsulated antibody but not the capsule wall of labeled microcapsule. The concentration of the surfactants at the time of measurement is properly chosen usually in the range of 0.01 to 2 V/V%, preferably 0.1 to 1 V/V%.

For the object of this invention, there cannot be used complement, polymyxin B, mellitin and the like which are conventionally used as capsule wall lysins for microcapsules such as liposome. Although the reason for this is not clear, it is conjectured, for example, as follows. The liposome membrane lysis of a capsule wall lysin such as complement, etc. does not destroy the structure of a liposome itself completely but makes a hole merely in a part of the membrane. Therefore, low-molecularweight substances (e.g. substances which can emit fluorescence, substrates for enzymes, etc.) can go in and out of the liposome freely through the hole, but high-molecular-weight substances such as antibody cannot pass through the hole and are kept in the liposome. Accordingly, the object of this invention cannot be achieved by using such a capsule wall lysin as complement in place of the surfactant.

As a microcapsule for the encapsulated antibody used in the measuring process of this invention, any microcapsule can be exemplified without particular restriction so long as it is more easily lysed by the surfactant than labeled microcapsule, though liposomes having such a property are preferred because of ease of preparation, and the like. As a method for preparing such liposomes, there can be exemplified well-known methods such as the voltexing method, sonication method, surfactant removal method, reverse-phase evaporation method (REV method), ethanol infusion method, ether infusion method, pre-vesicle method, French press extrusion method, $Ca^{2+}$ fusion method, annealing method, freeze thawing method, freeze drying method, W/O/W emulsion method, etc., and methods such as the stable plurilamellar vesicle method (SPLV method) recently reported by S. M. Gruner et al. [Biochemistry, 24, 2833 (1985)], and the method using a lipopolysaccharide as one constituent of membrane which has been reported by some of the present inventors (Japanese Patent Appln. Kokai (Laid-Open) No. 63-107742). Of these, particularly preferable are methods which permit preparation of unilamellar liposomes, for example, the surfactant removal method and the sonication method. As the main constituent of membrane of the liposome, there can be exemplified each or combinations of two or more of substances used as materials for membrane in preparation of conventional liposomes, i.e., natural lecithins (e.g. egg yolk lecithin, soybean lecithin, etc.) and phospholipids such as dipalmitoylphosphatidylcholine (DPPC), dimyristoylphosphatidylcholine (DMPC), distearoylphosphatidylcholine (DSPC), dioleoylphosphatidylcholine (DOPS), dimyrictoylphosphatidylethanolamine (DMPE), dipalmitoylphosphatidylglycerol (DPPG), dimyristoylphosphatidic acid (DMPA), egg yolk phosphatidylglycerol, etc.; mixtures of these substances and cholesterols; and combinations of the mixtures and polysaccharides, etc. Particularly preferable examples of the main constituent of membrane are lipids having a low Tc (e.g. egg yolk lecithin, etc.) and lipids which tend to be in hexagonal phase (e.g. phosphatidylethanolamine, acidic lipids, etc.).

The antibody contained in microcapsule in the encapsulated antibody of this invention is not critical, and any antibody may be used so long as it is an antibody to an analyte to be measured. That is, there may be used either polyclonal antibodies prepared by immunizing animals such as horse, cattle, sheep, rabbit, goat, rat, mouse, etc. with an analyte to be measured, according to a conventional method, for example, any of the methods described in Tadashi Matsuhashi et al. "Meneki Jikken-gaku Nyumon" 2nd. ed., GAKKAI-SHUPPAN CENTER Ltd., 1981; and E. Harlow et al. "Antibodies" Cold Spring Harbor Laboratory, 1988, pp.53-138, or monoclonal antibodies produced by Hybridomas obtained by fusing cells from a tumor line of mouse together with mouse spleen cells previously immunized with an analyte to be measured, according to the conventional method, i.e., the cell fusion method established by G. Köhler and C. Milstein (Nature, 256, 495, 1975). These polyclonal and/or monoclonal antibodies may be used singly or in proper combination of two or more thereof. Needless to say, they may be used, if necessary, after digesting them with an enzyme such as pepsin or papain into $F(ab')_2$, Fab' or Fab.

A method for preparing the encapsulated antibody of this invention is explained below in detail by taking the case of preparation of liposomes by the surfactant removal method.

First, such phospholipids and cholesterols described above are dissolved in a suitable organic solvent (e.g. chloroform, an ether, an alcohol, etc.), and the resulting solution is concentrated to dryness under reduced pressure and then sufficiently dried under reduced pressure in a desiccator. Subsequently, an aqueous surfactant solution (20 to 100 mM) is added to the lipid film thus formed and the film is uniformly dispersed thereinto. The surfactant used here includes, for example, those heretofore often used in the art, such as cholic acid, polyoxyethylene octylphenyl ether, octyl glucoside, etc., though surfactants having a high critical micelle concentration (CMC), such as octyl glucoside and the like are preferred. Next, if necessary, a lipopolysaccharide is added in powder form as it is or in solution, followed by adding thereto a solution of a desired antibody to be encapsulated (usually a solution having a concentration of 0.1 to 20 mgAb/ml, preferably 1 to 10 mgAb/ml), and the resulting mixture is sufficiently stirred. It is most preferable to remove the surfactant immediately after the stirring, and a method for the removal includes per se well-known methods such as dialysis, gel filtration, adsorption on resin, etc. As to the treatment conditions, the treatment time is 1 to 24 hours, and the treatment temperature may be properly chosen in the range of about 0° to about 70° C. though it is somewhat varied depending on the constituents of membrane of the liposome, etc. For removing the surfactant, gel filtration through Sepharose 4B (a trade name, Pharmacia AB), centrifugation, etc. are particularly advantageous because free antibody and the like can also be removed at the same time. The liposomes thus obtained are used or stored after being concentrated by ultrafiltration or the like so as to have a predetermined concentration. For making the sizes of the liposomes uniform, a method using a generally used polycarbonate membrane may be employed, though a gel filtration (using, for example, Sephacryl S-1000 (a trade name, Pharmacia AB)) is also effective.

Also when the encapsulated antibody of this invention is prepared by a method other than the surfactant removal method, it is sufficient that it is prepared similarly according to a per se well-known method or other methods for preparing liposomes.

As the labeled microcapsule used in the measuring process of this invention, any microcapsule can be exemplified without particular restriction so long as it is more difficultly lysed by the surfactant than the encapsulated antibody. Usually, a liposome having such a property is chosen because of ease of preparation, etc. As a method for preparing such liposomes, there can be exemplified all of the per se well-known preparation methods of liposomes previously exemplified for the microcapsule for the encapsulated antibody. As the constituents of membrane, there can be exemplified all of the per se well-known materials for membrane previously exemplified for the microcapsule for the encapsulated antibody. In particular, liposomes prepared from a lipid with a high phase transition temperature (e.g.

DPPC, DSPC, etc.) as a constituent of membrane by a method which permits preparation of multilamellar liposomes (e.g. SPLV method, REV method, etc.), are more preferable because they are more difficultly lysed by the surfactant than liposomes prepared from other methods and/or materials. Liposomes containing a labeled substance therein are thus prepared and an analyte to be measured is fixed on their surfaces by a conventional method. As the conventional method, when a water-soluble protein or the like is fixed, there can be used, for example, the crosslinking method, the lipid activation method, and the method using a lipopolysaccharide disclosed in Japanese Patent Appln. Kokai (Laid-Open) No. 63-107742. When a low-molecular-weight hapten is fixed, there can be used, for example, a method which comprises converting the hapten to a lipid derivative previously and then incorporating the liquid derivative into liposomes. Thus, the labeled microcapsules of this invention can easily be obtained. As the marker to be contained in the labeled microcapsules, any marker can be exemplified without particular restriction so long as it is a detectable marker usually used in an immunoassay method based on complement-dependent immune lysis of microcapsules. Typical examples of the marker are enzymes such as alkaline phosphatase, glucose-6-phosphate dehydrogenase, $\beta$-galactosidase, etc.; substances which can emit fluorescence, such as carboxyfluorescein, etc.; dyes such as Arsenazo III, 4-(2-pyridylazo)resorcinol, 2-(5-bromo-2-pyridylazo)-5-(N-propyl-N-sulfopropylamino)phenol sodium salt, etc.; luminescent substances such as luminol, bis(2,4,6-trichlorophenyl) oxalate, N-methylacridinium ester, etc.; and substances suitable as spin markers, which are represented, for example, by 2,2,6,6 tetramethylpiperidin-1-oxyl (TEMPO).

AS the complement used in the measuring process of this invention, there can be exemplified, without exception, all the complements usually used in the art, for example, complements derived from blood of animals such as human being, guinea pig, horse, sheep, etc. which have been properly purified by a conventional method.

It is sufficient that the concentration ranges of the reagents used in the measuring process of this invention and various antiseptics and the like optionally added in said process are properly selected from the concentration ranges which are usually employed for per se well-known reagents for immunoassay method based on complement-dependent immune lysis of microcapsules.

Buffers used in the measuring process of this invention include, for example, tris(hydroxymethyl)-aminomethane, Good's buffers, Veronal, etc. but are not limited thereto.

The reagent combination of this invention used for the measuring process of this invention is characterized by comprising the following two liquids.

First liquid: comprising encapsulated antibody, labeled microcapsules, and if necessary, a buffer, substances necessary for exhibition of the function of a marker contained in the labeled microcapsules (e.g. coenzyme, substrate for enzyme, etc.), an antiseptic, etc.

Second liquid: containing complement and if necessary, a substrate, coenzyme, buffer, antiseptic, etc.

As to the pH's of the reagent combination of this invention, the pH of the first liquid is properly chosen usually in the range of 6 to 9, preferably 7 to 8, and the pH of the second liquid is properly chosen usually in the range of 6 to 9, preferably 7 to 8. The pH's are adjusted using, for example, the buffers exemplified above.

The measuring process of this invention using the reagent combination of this invention is practiced, for example, as follows.

First, a surfactant capable of lysing the capsule wall of the encapsulated antibody but not the capsule wall of the labeled microcapsule is added to the first liquid together with a sample containing an analyte to be measured, to liberate the antibody. Then, the second liquid containing complement is allowed to act on the resulting mixture, followed by measurement by a conventional method. It is sufficient that the measurement itself is carried out according to a per se well-known immunoassay method based on complement-dependent immune lysis of microcapsules.

More specifically, first, a specimen for measurement is prepared by mixing a sample containing an analyte to be measured with a suitable surfactant. The specimen and the first liquid are properly mixed and then reacted with each other usually at 20° to 50° C., preferably 25° to 40° C., for 5 minutes to 1 hour. Subsequently, the resulting reaction solution is properly mixed with the second liquid, and the resulting mixture is subjected to reaction usually at 20° to 50° C., preferably 25° to 40° C., for 5 minutes to 1 hour. Then, the amount of the labeled substance liberated from the labeled microcapsules is measured by a per se well-known measuring method suitable for properties of the labeled substance. The concentration of the analyte to be measured in the sample is determined on the basis of the thus obtained amount of the labeled substance by using a calibration curve showing the relationship between the concentration of the analyte to be measured and the amount of the labeled substance liberated from the labeled microcapsules, said calibration curve previously prepared by subjecting several samples containing known concentrations of the analyte to be measured to the same procedure as described above.

In the above procedure, the order of reacting the first liquid and the second liquid with the specimen should not be changed. After mixing the specimen with the first liquid, they should be reacted with each other for a certain time. This is because measurement of the analyte to be measured becomes practically impossible when the first liquid and the second liquid are added in reverse order and reacted with the specimen, or when the first liquid and the second liquid are added at substantially the same time and reacted with the specimen.

As a method for measuring the amount of the marker, the following methods can be exemplified. For example, when the marker is an enzyme, it is measured according to, for example, any of the methods described, for instance, in Tsunehiko Kitagawa, Toshio Nanbara, Akio Tsuji, and Eiji Ishikawa "Koso Men-eki Sokuteiho", an extra issue No. 31 of Tanpakushitsu Kakusan Koso, pp. 51–63, KYORITSU-SHUPPAN Ltd., published on Sep. 10, 1987; and E. Harlow et al. "Antibodies" Cold Spring Harbor Laboratory, 1988, pp. 592-598. When the marker is a substance which can emit fluorescence, it is measured according to, for example, any of the methods described in Akira Kawano "Zusetsu Keikokotai" 1st ed. Soft Science, Inc., 1983; and R. M. Nakamura et al. "Immunoassays" Alan R. Liss, Inc., N.Y., 1980, pp. 10. When the marker is a luminescent substance, it is measured according to, for example, any of the methods described in Tsunehiro Kitazawa, Toshio Nanbara, Akio Tsuji and Eiji Ishikawa "Koso Men-eki Sokuteiho", an extra issue No. 31 of Tanpakushitsu Kakusan Koso, pp. 252-263, KYORITSU-shuppan Ltd., published on Sep. 10, 1987; and R. M. Nakamura et al. "Immunoassays" Alan R. Liss, Inc., New York, 1980, pp. 174-176. When the marker is a spin marker, it is measured according to, for example, any of the methods described in Tsunehiro Kitagawa, Toshio Nanbara, Akio Tsuji and Eiji Ishikawa "Koso Men-eki Sokuteiho" an extra issue No. 31 of Tanpakushitsu Kakusan Koso, pp. 264-271, KYORITSU-SHUPPAN Ltd., published on Sep. 10, 1987; and R. M. Nakamura et al. "Immunoassays" Alan R. Liss Inc., N.Y., 1980, pp. 213-218.

As an analyte which can be measured by the measuring process of this invention, there can be exemplified, without particular restriction, any substance which permits preparation of an antibody thereto, or any antibody produced in a living body. Typical examples of the analyte to be measured include proteins, lipids, hormones, drugs and specific substances, which are contained in body fluids such as serum, blood, plasma, urine, etc. More specific examples of the analyte to be measured include tumor markers such as α-fetoprotein (AFP), CA19-9, prostate gland specific antigen (PSA), carcinoembryonic antigen (CEA), and the like; hormones such as insulin, human chorionic gonadotropin (hCG), thyroxine (T4), triiodothyronine (T3), prolactin, thyroid stimulating hormone (TSH), and the like; drugs such as digoxin, phenytoin, morphine, nicotine, and the like; and antibodies such as anti-Toxoplasma antibody, and the like.

This invention is illustrated below in further detail with reference to Examples, which are not by way of limitation but by way of illustration.

EXAMPLES

Referential Example 1

Preparation of Encapsulated Antibody

In a round bottom flask were placed 2 ml of a 20 mM solution of egg yolk lecithin in chloroform and 2 ml of a 20 mM solution of cholesterol in chloroform, and mixed. Then, the solvent was distilled off by means of a rotary evaporator, followed by drying under reduced pressure in a desiccator for about 2 hours, whereby a lipid thin film was formed on the interior surface of the flask. To the lipid thin film were added 0.6 ml of a 200 mM aqueous n-octyl glucoside solution (containing 6.6 mg/ml of lipopolysaccharide) and 0.01 M N-2-hydroxyethylpiperazine-N'-2-ethanesulfonic acid (HEPES) buffer (pH 7.4), and the resulting mixture was stirred in a Vortex mixer until uniform dispersion was achieved. Subsequently, 0.3 ml of anti-human T4 serum (5 mg Ab/ml) was added and stirred The resulting mixture was placed in a dialyzing tube and dialyzed against 0.01M HEPES buffer (pH 7.4) for 1 hour, after which the liposome suspension thus obtained was purified by ultra-centrifugation (35,000 r.p.m., 40 mm×5). The pellets thus obtained were suspended in 5 ml of 0.01 M HEPES buffer (pH 7.4) to obtain encapsulated anti-T4 antibody.

EXAMPLE 1

Measurement of Human T4

Specimens

Mixtures of 50 μl of a 0.1% bovine serum albumin solution containing a predetermined concentration of human T4 and 150 μl of a pretreating agent (a 0.16 N NaOH solution containing 2.7% polyoxyethylene (10) octylphenyl ether)

Liquid Reagents

| Reagent 1 (R1): | |
|---|---|
| A solution of | |
| T4-labeled liposomes | 11 μmol/ml |
| (containing glucose-6- | (in terms of |
| phosphate dehydrogenase) | cholesterol) |
| the encapsulated anti-T4 | 2 μmol/ml |
| antibody obtained in | (in terms of |
| Referential Example 1 | cholesterol) |
| oxidized form nicotinamide | 3.2 mg/ml |
| adenine dinucleotide (NAD) | |
| in 50 mM 3-(N-morpholino)-2- | |
| hydroxypropanesulfonic | |
| acid buffer (pH 7.4) | |
| Reagent 2 (R2): | |
| A solution of | |
| a complement (guinea pig | 0.25 ml/ml |
| fresh serum) | |
| glucose-6-phosphate (G-6-P) | 6.5 mg/ml |
| in 50 mM tris(hydroxymethyl)aminomethane | |
| buffer (pH 7.4) | |

Procedure

To 20 μl of each specimen was added 200 μl of R1 and the resulting mixture was incubated at 37° C. for 5 minutes. Then, 100 μl of R2 was added, and after further incubation at 37° C. for 5 minutes, the change of absorbance at 340 nm was measured.

Results

The calibration curve thus obtained is shown in FIG. 1. It was prepared by plating absorbance (OD$_{340}$nm) on the axis of ordinate corresponding to individual T4 concentrations (μg/dl) on the axis of abscissa.

As is clear from FIG. 1, a satisfactory calibration curve can be obtained by the immunoassay method based on complement-dependent immune lysis of microcapsules of this invention which uses the reagent combination for immunoassay method based on complement-dependent immune lysis of microcapsules of this invention.

T4 was measured by use of the same reagent as described above by the same procedure as described above, except for using as specimens, mixtures of 50 μl of each of control sera I, II and III of Bio-Rad Laboratories and 150 μl of the aforesaid pretreating agent. The amount of T4 in each control serum was determined using the calibration curve obtained in the results obtained are shown in Table 1.

TABLE 1

| Control serum | Measured value (μg/dl) | Values indicated by Bio-Rad Laboratories (μg/dl) |
|---|---|---|
| I | 6.0 | 3.4-5.2 |
| II | 10.4 | 7.7-10.1 |
| III | 14.8 | 13.2-16.8 |

As is clear from the results shown in Table 1, satisfactory measurement results can be obtained by the process of this invention.

EXAMPLE 2

Stability Test on Reagent Liquids

Specimens

Mixtures of 50 μl of a 0.1% bovine serum albumin solution containing a T4 concentration of 0, 10 g/dl and 150 μl of the same pretreating solution as in Example 1.

Liquid Reagent

R1: a liquid reagent prepared in the same manner as in Example 1 and stored at 15° C. for a predetermined number of days.
R2: the same as in Example 1.

Procedure

To 20 μl of each specimen was added 600 μl of R1 and the resulting mixture was incubated at 37° C. for 5 minutes. Then, 300 μl of R2 was added, and after further incubation at 37° C. for 5 minutes, the change of absorbance at 340 nm was measured.

Results

The measurement results are shown in Table 2.

TABLE 2

| T4 concentration (μg/dl) | Number of storage days (15° C.) | | |
|---|---|---|---|
| | Immediately after preparation | 2nd day | 5th day |
| | Measured value (OD $_{340\ nm}$) | | |
| 0 | 0.722 | 0.700 | 0.700 |
| 10 | 0.455 | 0.450 | 0.440 |
| 25 | 0.221 | 0.215 | 0.217 |

As is clear from the results shown in Table 2, the reagents of this invention have a good stability.

When T4 was measured by using as R1 a liquid reagent prepared by use of a conventional antibody solution in place of the encapsulated antibody of this invention, there was no difference among measured values (OD $_{340\ nm}$) obtained for the specimens in the case where the T4 concentration was 0, 10 or 25 μg/dl (data not shown). Thus, it was clear that this liquid reagent was of no practical use.

EXAMPLE 3

Measurement of Human T4 in Serum

Specimens

Mixtures of 50 μl of each of fresh sera of 25 human beings and 150 μl of a pretreating agent (a 0.16 N NaOH solution containing 2.7% polyoxyethylene (10) octylphenyl ether).

Liquid Reagents

R1: the same as in Example 1.
R2: the same as in Example 1.

Procedure

The same as in Example 1.

COMPARATIVE EXAMPLE 1

Measurement of T4 in human serum

T4 was measured for the same fresh sera of 25 human beings as used in Example 3, by using a commercially available reagent for measuring T4 (Amerlex T4, mfd. by Amersham International plc.). The measurement was carried out according to the standard procedure described in the instructions.

In FIG. 2 is shown a correlational graph prepared on the basis of measured values obtained by Example 3 and Comparative Example 1.

The results of statistical processing of the measured values obtained by Example 3 and Comparative Example 1 are shown below:

| Correlation coefficient | $\gamma = 0.9806$ |
|---|---|
| Regression line formula | $Y = 1.057X - 0.75$ | wherein
Y: the measured value obtained by Example 3
X: the measured value obtained by comparative Example 1

As is clear from the above results, the measured values of T4 obtained by measuring process of this invention were in good correlation with those obtained by a conventional method.

As described above, the present invention provides an improved immunoassay method based on complement-dependent immune lysis of microcapsules which uses liquid regents of novel forms. The measuring process of this invention is markedly effective in that it permits application to autoanalyzers which is difficult for conventional methods. Therefore, this invention contributes greatly to the art.

What is claimed is:

1. A liquid reagent used for an immunoassay method based on complement-dependent immune lysis of microcapsules comprising
   (a) first liposome microcapsules having an analyte immobilized on surfaces thereof and containing a marker therein, wherein said first liposome microcapsules are capable of being lysed by complement-dependent immune lysis, and
   (b) second liposome microcapsules having different capsule walls from said first liposome microcapsules and encapsulating an antibody specific to said analyte, wherein the capsule walls of said second liposome microcapsules are more easily lysed by a surfactant than the capsule walls of said first liposome microcapsules.

2. A liquid reagent according to claim 1, wherein said second liposome microcapsule is a liposome prepared by a surfactant removal method.

3. An immunoassay reagent combination used for an immunoassay method based on complement-dependent immune lysis of microcapsules comprising
   (i) a first liquid comprising
      (a) first liposome microcapsules having an analyte immobilized on surfaces thereof and containing a marker therein, wherein said first liposome microcapsules are capable of being lysed by complement-dependent immune lysis, and
      (b) second liposome microcapsules having different capsule walls from said first liposome microcapsules and encapsulating an antibody specific to said analyte, wherein the capsule walls of said second liposome microcapsules are more easily lysed by a surfactant than the capsule walls of said first liposome microcapsules, and
   (ii) a second liquid containing complement.

4. An immunoassay reagent combination according to claim 3, wherein said second liposome microcapsule is a liposome prepared by a surfactant removal method.

5. An immunoassay method based on complement-dependent immune lysis of microcapsules comprising
a first step of reacting a sample analyte and a surfactant with a first liquid comprising,
(a) first liposome microcapsules having an analyte immobilized on surfaces thereof and containing a marker therein, wherein said first liposome microcapsules are capable of being lysed by complement-dependent immune lysis, and
(b) second liposome microcapsules having different capsule walls from said first liposome microcapsules and encapsulating an antibody specific to said analyte, wherein the capsule walls of said second liposome microcapsules are more easily lysed by said surfactant than the capsule walls of said first liposome microcapsules, wherein said surfactant is present in a concentration sufficient to lyse said second liposome microcapsules but not said first liposome microcapsules, a second step of reacting the resulting reaction solution with a second liquid containing complement, and a third step of measuring the amount of the marker liberated by the second step as an indication of the amount of said sample analyte.

6. An immunoassay method according to claim 5, wherein said second liposome microcapsule encapsulating an antibody is a liposome prepared by a surfactant removal method.

7. An immunoassay method according to claim 5, wherein the marker is selected from the group consisting of an enzyme, a substance which can emit fluorescence, a dye, a luminescent substance and a spin marker.

8. An immunoassay method according to claim 5, wherein the marker is an enzyme.

9. An immunoassay method according to claim 8, wherein the enzyme is glucose-6-phosphate dehydrogenase.

* * * * *

UNITED STATES PATENT AND TRADEMARK OFFICE
CERTIFICATE OF CORRECTION

PATENT NO.: 5,221,613
DATED : June 22, 1993
INVENTOR(S): Masaaki KIDA et al.

It is certified that error appears in the above-identified patent and that said Letters Patent is hereby corrected as shown below:

On the title page, Item [75], change "Kazunisa" to --Kazuhisa--.

Signed and Sealed this

Tenth Day of May, 1994

Attest:

BRUCE LEHMAN

*Attesting Officer*        *Commissioner of Patents and Trademarks*